(12) United States Patent
Kemp et al.

(10) Patent No.: US 9,283,326 B2
(45) Date of Patent: Mar. 15, 2016

(54) AUTO-INJECTOR

(75) Inventors: Thomas Mark Kemp, Ashwell (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 415 days.

(21) Appl. No.: 13/877,492

(22) PCT Filed: Oct. 6, 2011

(86) PCT No.: PCT/EP2011/067493
§ 371 (c)(1),
(2), (4) Date: Apr. 3, 2013

(87) PCT Pub. No.: WO2012/045831
PCT Pub. Date: Apr. 12, 2012

(65) Prior Publication Data
US 2013/0190721 A1 Jul. 25, 2013

Related U.S. Application Data

(60) Provisional application No. 61/432,260, filed on Jan. 13, 2011.

(30) Foreign Application Priority Data

Oct. 8, 2010 (EP) ..................................... 10186995

(51) Int. Cl.
*A61M 5/32* (2006.01)
*A61M 5/20* (2006.01)

(52) U.S. Cl.
CPC ........... *A61M 5/3232* (2013.01); *A61M 5/2033* (2013.01); *A61M 5/3202* (2013.01); *A61M 5/326* (2013.01); *A61M 2005/206* (2013.01); *A61M 2005/2013* (2013.01)

(58) Field of Classification Search
CPC ............ A61M 5/2033; A61M 5/3232; A61M 5/3202; A61M 2005/2013; A61M 2005/206; A61M 5/326
See application file for complete search history.

(56) References Cited

U.S. PATENT DOCUMENTS

2002/0095120 A1 7/2002 Larsen et al.
2006/0224124 A1 10/2006 Scherer
2007/0027430 A1* 2/2007 Hommann ..................... 604/207

FOREIGN PATENT DOCUMENTS

EP 1743666 1/2007
WO 2009/062508 5/2009

OTHER PUBLICATIONS

International Search Report for Int. App. No. PCT/EP2011/067493, completed Feb. 8, 2012.

*Primary Examiner* — Theodore Stigell
(74) *Attorney, Agent, or Firm* — Fish & Richardson P.C.

(57) ABSTRACT

The invention refers to an auto-injector and to a method for operating it, the auto-injector comprising of a tubular chassis; a carrier subassembly comprising a tubular carrier slidably arranged in the chassis, the carrier containing a syringe with a hollow injection needle, a drive spring and a plunger for forwarding load of the drive spring to a stopper of the syringe; a wrap-over trigger sleeve arranged over the distal end (D) of the auto-injector; the trigger sleeve extending at least almost over the whole length of the auto-injector; a control spring arranged around the carrier; first interlock means for coupling a proximal end of the control spring to either the carrier for advancing it for needle insertion or to the chassis for needle retraction; second interlock means arranged for releasing the drive spring for injection; third interlock means arranged for coupling the chassis to the carrier for joint axial translation relative to the trigger sleeve; and fourth interlock means arranged for coupling a distal end of the control spring to either the carrier for needle retraction or to the trigger sleeve otherwise.

20 Claims, 10 Drawing Sheets

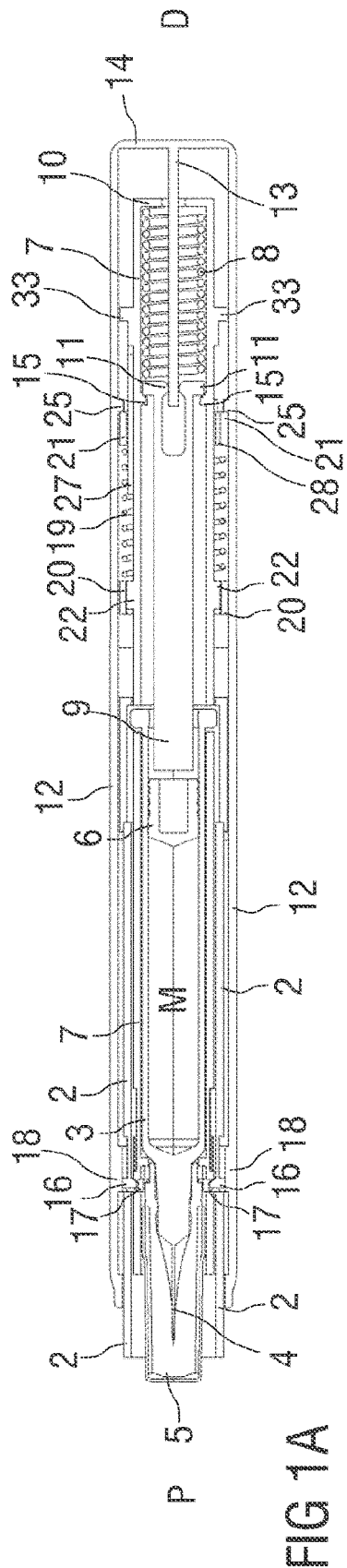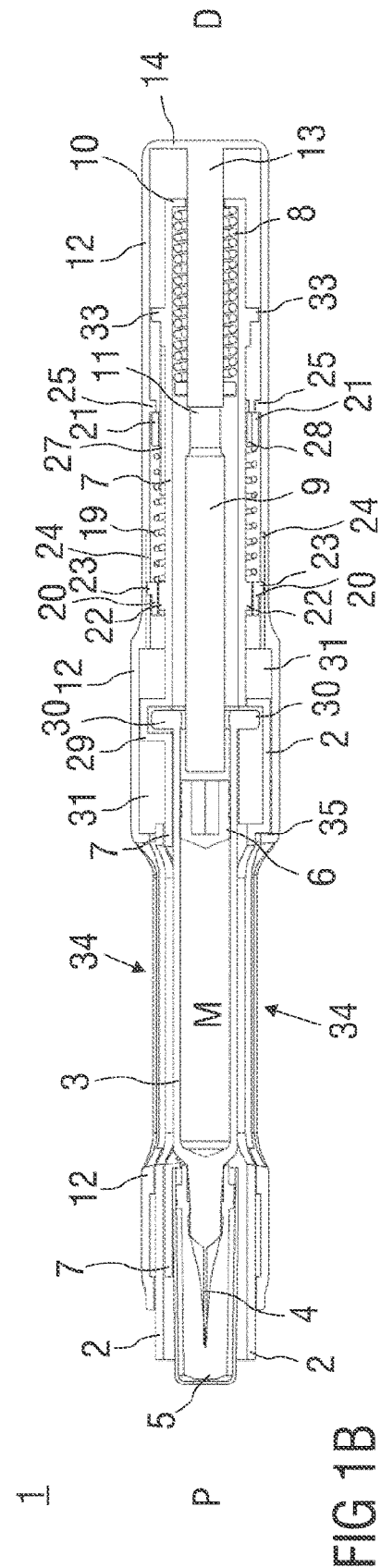
FIG 1A
FIG 1B

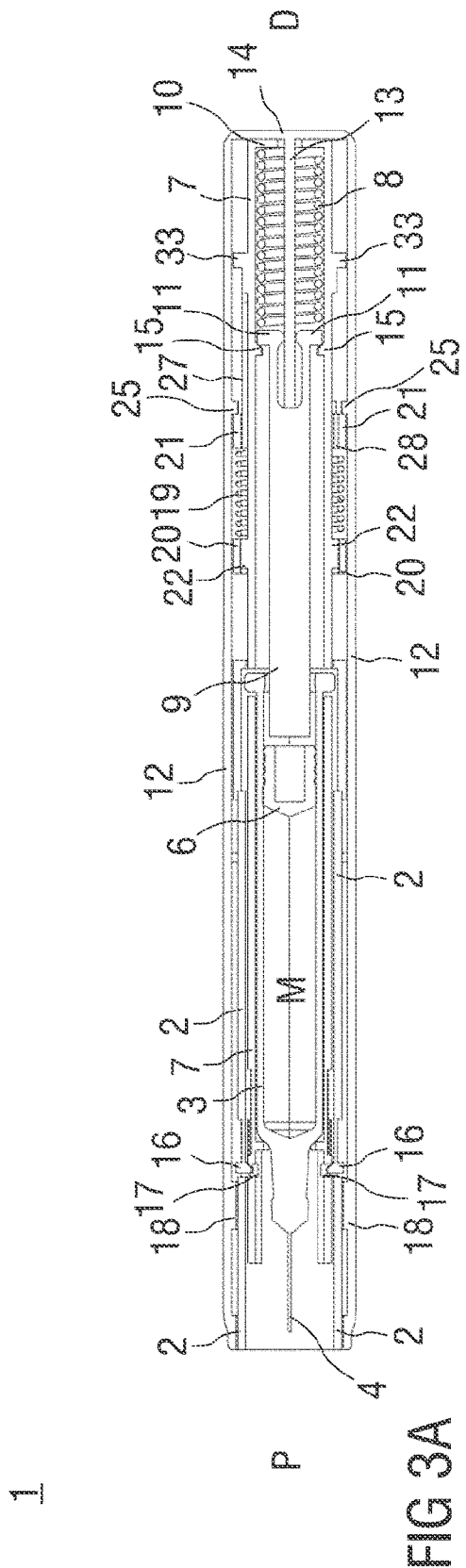
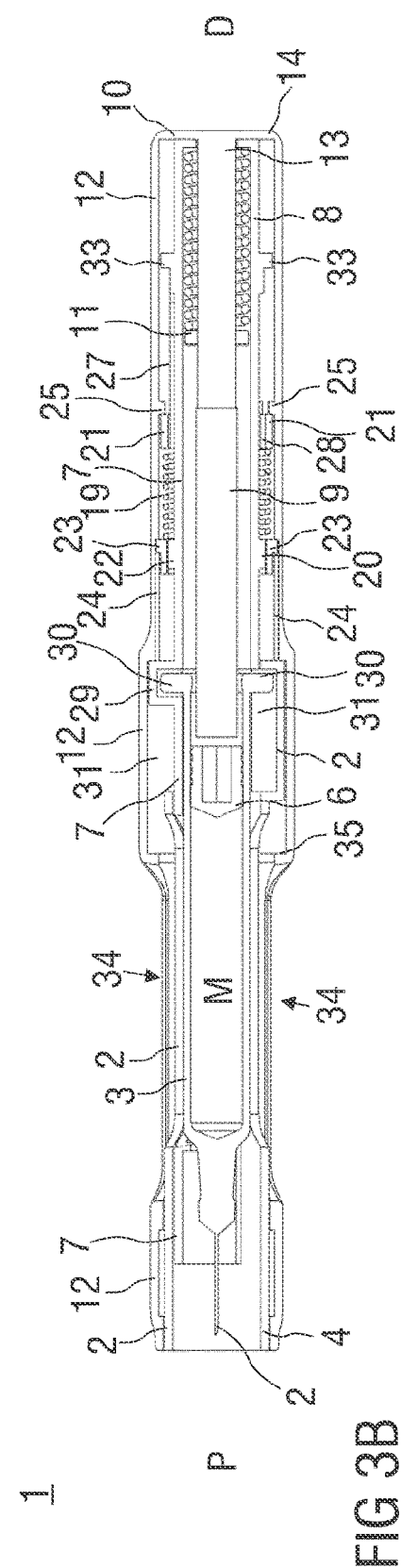
FIG 3A
FIG 3B

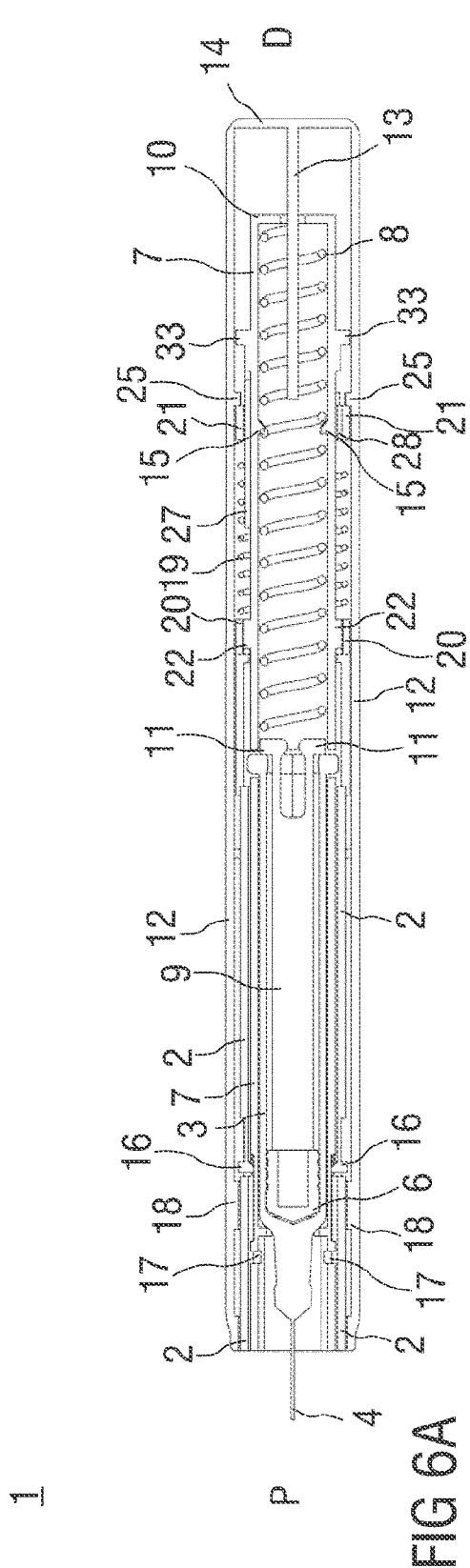
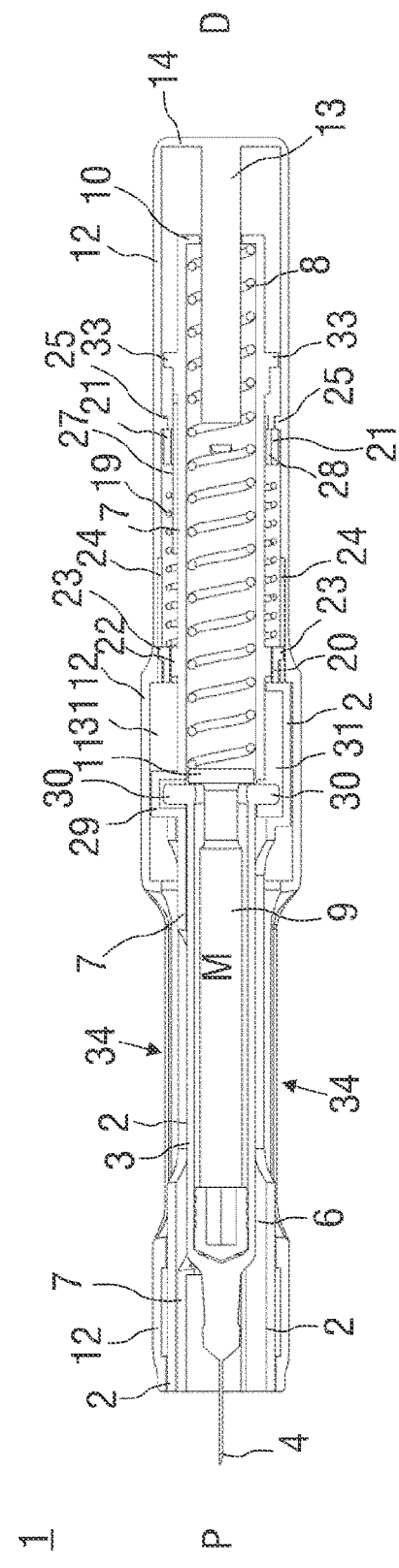
FIG 6A
FIG 6B

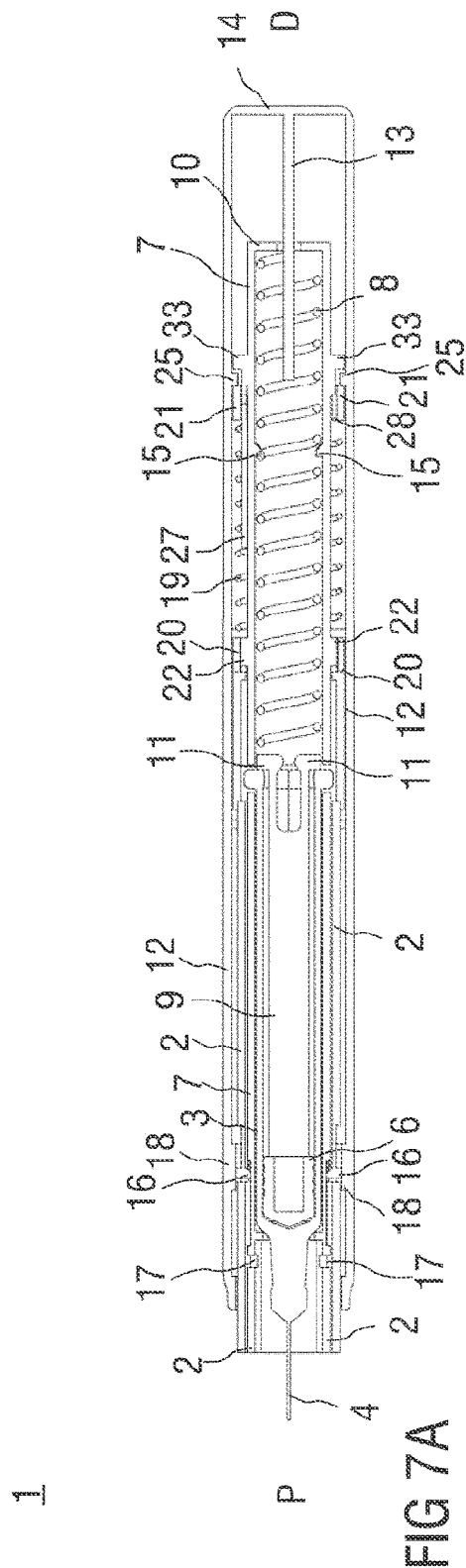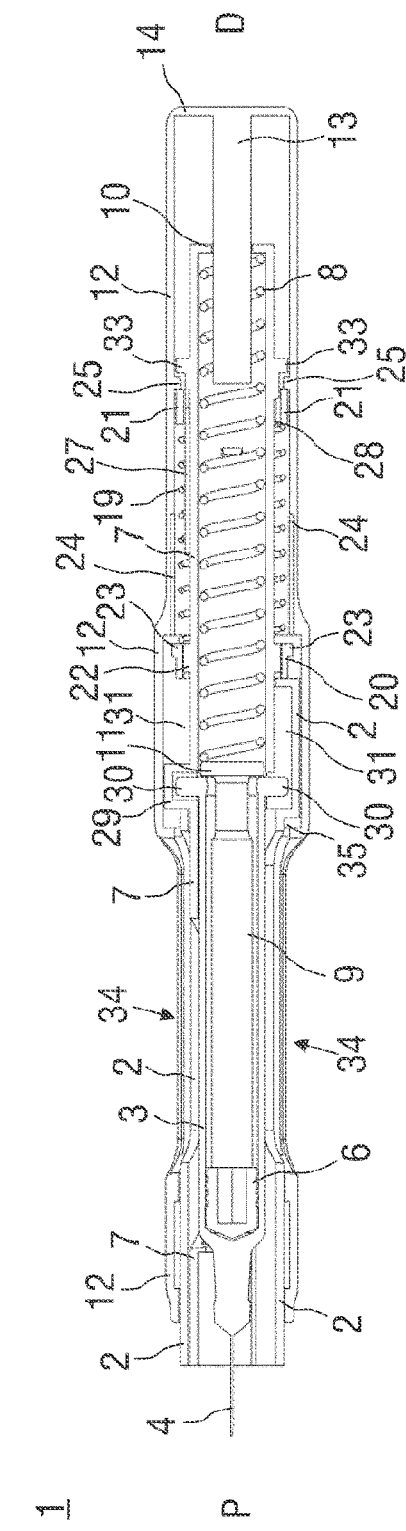
FIG 7A
FIG 7A

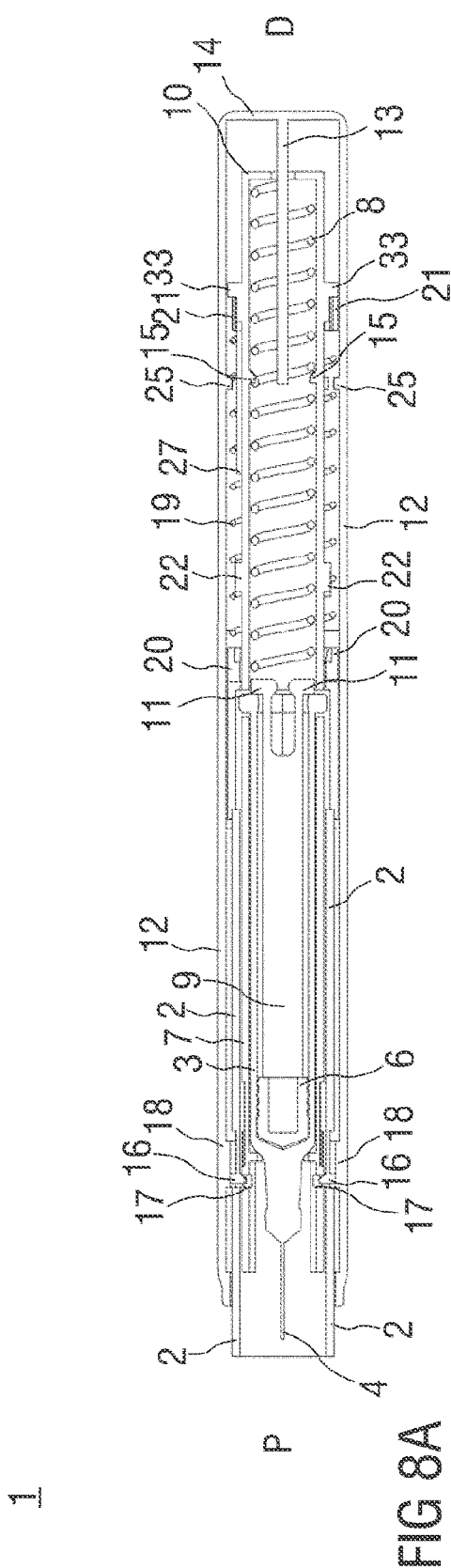
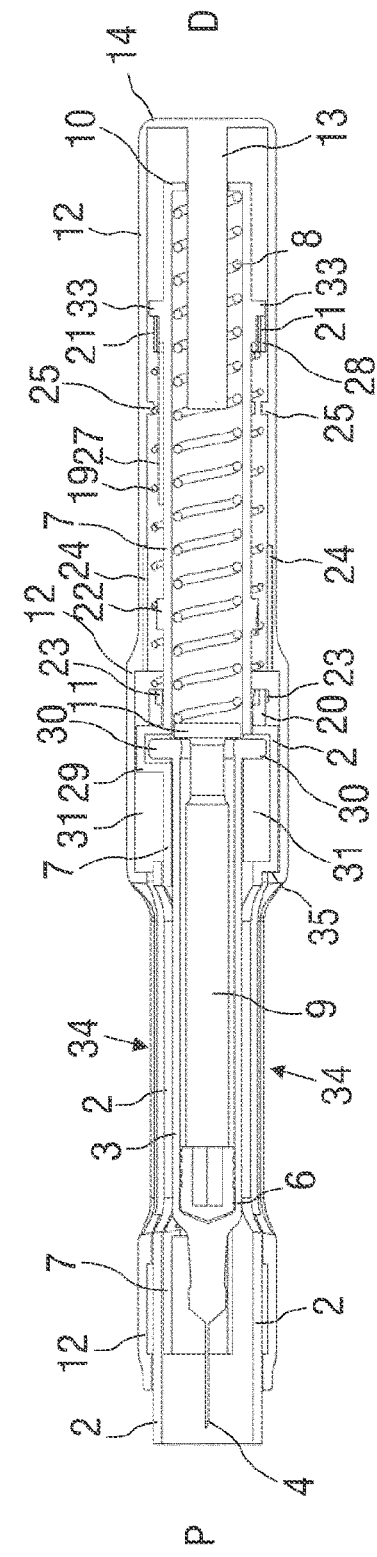
FIG 8A
FIG 8B

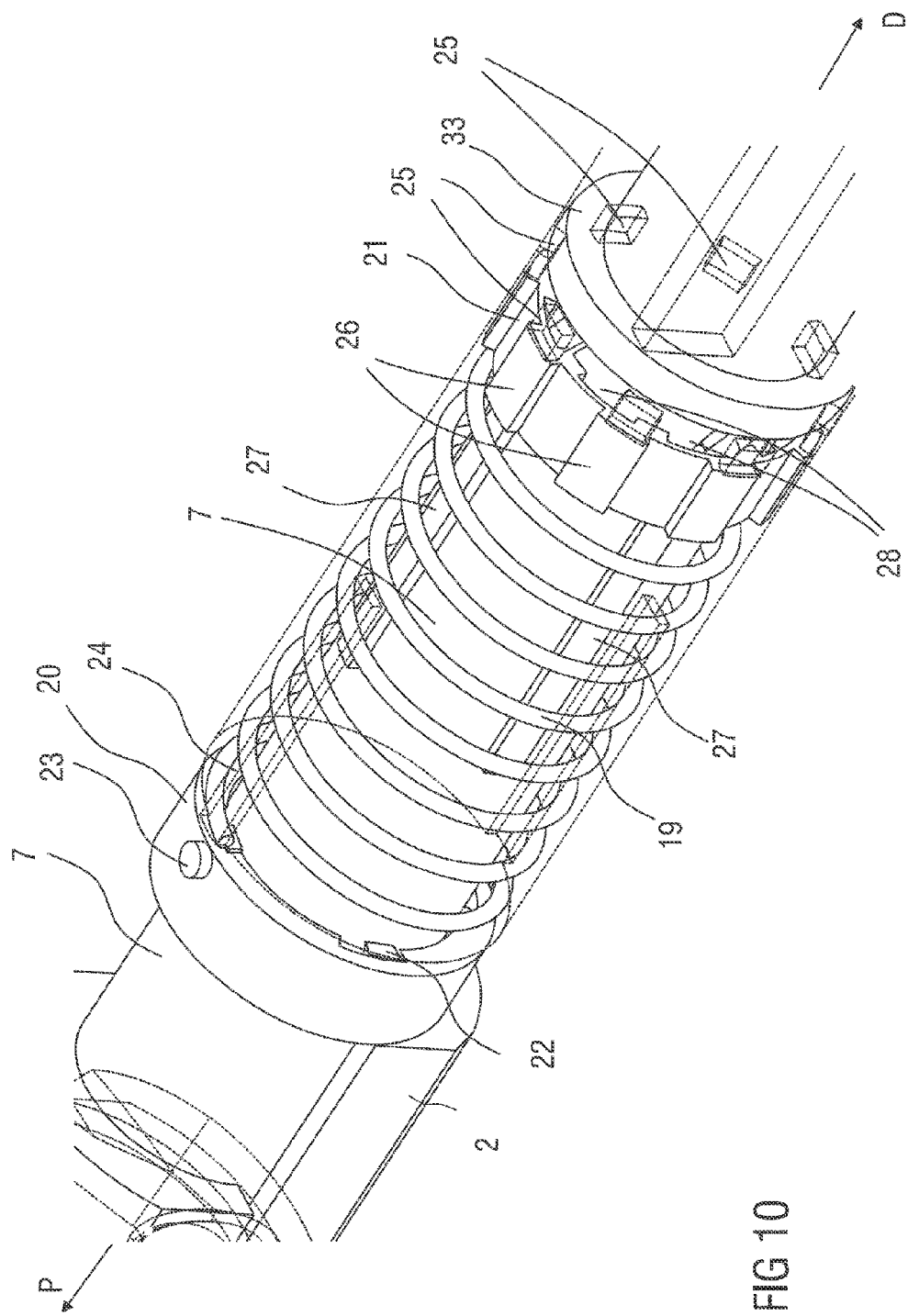

AUTO-INJECTOR

CROSS REFERENCE TO RELATED APPLICATIONS

The present application is a U.S. National Phase Application pursuant to 35 U.S.C. §371 of International Application No. PCT/EP2011/067493 filed Oct. 6, 2011, which claims priority to European Patent Application No. 10186995.6 filed Oct. 8, 2010 and U.S. Provisional Patent Application No. 61/432,260 filed Jan. 13, 2011. The entire disclosure contents of these applications are herewith incorporated by reference into the present application.

TECHNICAL FIELD

The invention relates to an auto-injector for administering a dose of a liquid medicament according to the preamble of claim 1 and to a method for operating an auto-injector.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

High viscosity medicaments require high forces for expelling them through the relatively thin injection needle. To achieve these forces strong drive springs are needed. This can lead to a high impact felt by the user when inserting the needle into the skin and to high forces felt by the user when triggering the injection.

SUMMARY

It is an object of the present invention to provide an improved auto-injector and an improved method for operating an auto-injector.

The object is achieved by an auto-injector according to claim 1 and by a method according to claim 9.

In the context of this specification the term proximal refers to the direction pointing towards the patient during an injection while the term distal refers to the opposite direction pointing away from the patient.

Preferred embodiments of the invention are given in the dependent claims.

According to the invention an auto-injector for administering a dose of a liquid medicament comprises:
    a tubular chassis,
    a carrier subassembly comprising a tubular carrier slidably arranged relative to the chassis and partially arranged in the chassis, the carrier containing a syringe with a hollow injection needle, a drive spring and a plunger for forwarding load of the drive spring to a stopper of the syringe, wherein the syringe is locked for joint axial translation with the carrier,
    a wrap-over trigger sleeve arranged over the distal end of the auto-injector, the trigger sleeve extending at least almost over the whole length of the auto-injector,
    a control spring arranged around the carrier,
    first interlock means for coupling a proximal end of the control spring to either the carrier for advancing it for needle insertion or to the chassis for needle retraction depending on the relative axial position of the carrier and the trigger sleeve,
    second interlock means arranged for releasing the drive spring for injection when the carrier has at least almost reached an injection depth during needle insertion,
    third interlock means arranged for coupling the chassis to the carrier for joint axial translation relative to the trigger sleeve, wherein the third interlock means are arranged to decouple the chassis from the carrier upon translation of the trigger sleeve in proximal direction relative to the chassis thus releasing the control spring for needle insertion,
    fourth interlock means arranged for coupling a distal end of the control spring to either the carrier for needle retraction or to the trigger sleeve otherwise.

The carrier subassembly with the integrated drive spring allows for employing a strong drive spring without any impact on the user when triggering the auto-injector or during needle insertion since these actions are achieved or opposed by the control spring which can be specified considerably weaker than the drive spring. This allows for delivering highly viscous medicaments.

Releasing the drive spring upon the needle reaching an injection depth avoids a so called wet injection, i.e. medicament leaking out of the needle which is a problem in conventional art auto-injectors, where both needle insertion and injection are achieved by pushing on the stopper.

The auto-injector according to the invention has a particularly low part count compared to most conventional auto-injectors thus reducing manufacturing costs. The arrangement with separate control spring and drive spring for fluid injection allows for using one design for different viscosity liquids by just changing the drive spring, and for different volumes just by changing the length of the plunger. This is an advantage over conventional art designs where the main spring also powers needle insertion and/or retraction.

In an initial as delivered state of the auto-injector the proximal end of the control spring is coupled to the carrier by the first interlock means, release of the drive spring is prevented by the second interlock means, decoupling of the chassis from the carrier is prevented by the third interlock means and the distal end of the control spring is coupled to the trigger sleeve.

In order to trigger an injection the auto-injector has to be pressed against an injection site, e.g. a patient's skin. A user, e.g. the patient or a caregiver, grabs the wrap-over trigger sleeve with their whole hand and pushes the chassis protruding from the proximal end against the injection site. The auto-injector is thus particularly well suited for people with dexterity problems since, as opposed to conventional art auto-injectors, triggering does not require operation of small buttons by single fingers. Instead, the whole hand is used.

When pushed against the injection site, the trigger sleeve translates in proximal direction relative to the chassis against the force of the control spring. The third interlock means disengages when the trigger sleeve is at least almost fully translated thereby releasing the control spring for advancing the carrier subassembly for needle insertion.

As the needle translated with the carrier subassembly at least almost reaches an injection depth the drive spring is released by the second interlock means. The drive spring advances the plunger and the stopper in proximal direction for at least partially delivering the medicament.

If the auto-injector is removed from the injection site after the stopper has bottomed out in the syringe or mid injection, the trigger sleeve is translated in distal direction under load of the control spring relative to the carrier subassembly.

As the trigger sleeve reaches a defined position relative to the carrier during that motion the proximal end of the control spring is decoupled from the carrier and coupled to the chassis by the first interlock means. Furthermore the distal end of the control spring is decoupled from the trigger sleeve and coupled to the carrier by the fourth interlock means.

As the control spring now pushes against the chassis in proximal direction and against the carrier in distal direction the carrier subassembly is retracted into the chassis into a needle safe position by the control spring.

The first interlock means may comprise a proximal collar for transmitting load of the proximal end of the control spring. The proximal collar is engaged on a thread on the carrier in the initial state. The proximal collar has a pin arranged to be splined to a first longitudinal groove in the trigger sleeve in the initial state so as to prevent rotation of the proximal collar and to couple it to the carrier by pushing on the thread. Upon translation of the chassis and carrier in proximal direction relative to the trigger sleeve during removal of the auto-injector from the injection site the pin travels beyond a proximal end of the first longitudinal groove, e.g. into a clearance and is thus released so the proximal collar can rotate and translate relative to the carrier under load of the control spring, i.e. the proximal collar is decoupled from the carrier.

The control spring translates the proximal collar in proximal direction until it abuts against the chassis.

The second interlock means may comprise two resilient arms arranged distally on the plunger. The resilient arms exhibit a thrust face for a proximal end of the drive spring. A distal end of the drive spring acts against the carrier, e.g. a carrier end face. A first boss protrudes from a distal trigger end face of the trigger sleeve in proximal direction into the carrier. The first boss is arranged between the two resilient arms in the initial state thus preventing them from flexing towards each other. A number of protrusions are arranged in the carrier for respectively catching one of the resilient arms in a manner to prevent translation of the plunger in proximal direction in the initial state. During needle insertion the carrier is translated in proximal direction relative to the trigger sleeve. The boss is thus removed from between the resilient arms when the carrier has at least almost reached the injection depth during needle insertion thus allowing the resilient arms to flex inwards due to their ramped engagement to the protrusions under load of the drive spring. Hence, the plunger is released for advancing the stopper and delivering the medicament.

A ramped engagement in the terminology of this specification is an engagement between two components with at least one of them having a ramp for engaging the other component in such a manner that one of the components is flexed aside when the components are axially pushed against each other provided this component is not prevented from flexing aside.

The third interlock means may comprise at least one resilient clip on the chassis engaged in a respective aperture in the carrier in the initial state for locking the chassis to the carrier. At least one second boss is arranged in the trigger sleeve for outwardly supporting the resilient clip so as to prevent the resilient clip from flexing outwards and disengaging the carrier from the chassis in the initial state. The second boss is removed from behind the resilient clip on translation of the trigger sleeve in proximal direction relative to the chassis when the auto-injector is being pushed against the injection site. The resilient clip is subsequently flexed outwards due to its ramped engagement with the carrier under load of the control spring releasing the control spring for needle insertion.

The fourth interlock means may comprise a distal collar for transmitting load of the distal end of the control spring. The distal collar and the trigger sleeve may be coupled by a bayonet fitting restricting translation of the distal collar relative to the trigger sleeve in distal direction in at least one locked angular position of the distal collar. In at least one unlocked angular position of the bayonet fitting the distal collar can translate relative to the trigger sleeve in distal direction. The respective angular position is determined by a splined engagement of the distal collar with the carrier. The distal collar is in the locked angular position in the initial state and remains there due to the splined engagement. Upon translation of the chassis and carrier in proximal direction during removal of the auto-injector from the injection site the distal collar is rotated into the unlocked angular position by the splined engagement thus decoupling it from the trigger sleeve. The distal collar is subsequently translated in distal direction relative to the trigger sleeve under load of the control spring into a position where it abuts against an external shoulder on the carrier which is then translated in distal direction for retraction.

The bayonet fitting may comprise at least one circumferentially arranged third boss, preferably a number of equally spaced third bosses on the inner surface of the trigger sleeve and a corresponding number of circumferentially arranged fourth bosses on the outer surface of the distal collar. In the locked angular position corresponding pairs of third bosses and fourth bosses are essentially aligned in a manner to abut against each other thus preventing translation of the distal collar in distal direction. Upon translation of the chassis and carrier in proximal direction during removal of the auto-injector from the injection site the distal collar is rotated by the splined engagement into the unlocked angular position, thereby misaligning the corresponding pairs of third bosses and fourth bosses in a manner to allow translation of the distal collar in distal direction, e. g. by the third bosses passing through gaps between the fourth bosses and vice versa.

The splined engagement may comprise at least one longitudinal spline on the carrier engaged with a respective second longitudinal groove on the inner surface of the distal collar. The spline is essentially parallel for maintaining the distal collar in the locked angular position but ends with a lead screw thread near its distal end for rotating the distal collar into the unlocked angular position. The second longitudinal groove is guided on an essentially parallel part of the spline in the initial state for maintaining the distal collar in the locked angular position until removal of the auto-injector from the injection site. The second longitudinal groove is moved along the spline upon translation of the chassis and carrier in proximal direction when the auto-injector is removed from the injection site and enters the lead screw thread for rotating the distal collar into the unlocked angular position.

It goes without saying that splines or threads between two components may be arranged either way with the spline on the first and the groove on the other component or the other way round.

In order to ensure needle safety under inertial forces, e.g. when the auto-injector is heavily shaken after use a snap feature may be provided between the chassis and the carrier for locking them together when the carrier is refracted into the needle safe position.

A detent mechanism may be arranged for opposing translation of the chassis relative to the trigger sleeve for triggering needle insertion thus providing the auto-injector with a two-stage firing mechanism.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 is an auto-injector with a syringe in an initial state prior to actuation, FIG. 3 is the auto-injector with a sleeve trigger button fully depressed, FIG. 6 is the auto-injector with the syringe emptied, FIG. 7 is the auto-injector removed from the injection site after the end of injection, FIG. 8 is the auto-injector with the syringe and needle retracted into a needle safe position, FIG. 10 is another detail view of the auto-injector with the control spring, the proximal collar and the distal collar in the state as in FIG. 7.

Corresponding parts are marked with the same reference symbols in all figures.

DETAILED DESCRIPTION

Figure 2A:
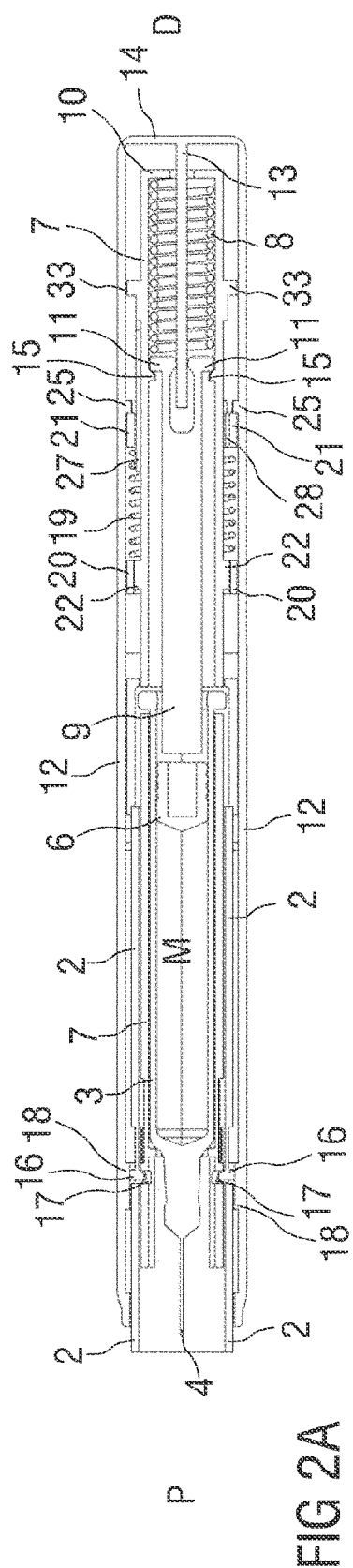
FIG. 2 is the auto-injector with a protective needle shield removed and pushed against an injection site.

FIG. 1 shows two longitudinal sections in different section planes of an auto-injector 1, the different section planes approximately 90° rotated to each other, wherein the auto-injector 1 is in an initial state prior to starting an injection. The auto-injector 1 comprises a chassis 2. A syringe 3, e.g. a Hypak syringe, with a hollow injection needle 4 is arranged in a proximal part of the auto-injector 1. When the auto-injector 1 or the syringe 3 is assembled a protective needle shield 5 is attached to the needle 4. A stopper 6 is arranged for sealing the syringe 3 distally and for displacing a liquid medicament M through the hollow needle 4. The syringe 3 is held in a tubular carrier 7 and supported at its proximal end therein. The carrier 7 is slidably arranged in the chassis 2.

A drive spring 8 in the shape of a compression spring is arranged in a distal part of the carrier 7. A plunger 9 serves for forwarding the force of the drive spring 8 to the stopper 6.

The drive spring 8 is loaded between a distal carrier end face 10 of the carrier 7 and a thrust face on two resilient arms 11 arranged distally on the plunger 9.

A wrap-over trigger sleeve 12 is arranged over the distal end D of the auto-injector 1 extending almost over the whole length of the auto-injector 1. A first boss 13 protrudes from a distal trigger end face 14 of the trigger sleeve 12 in proximal direction P between the two resilient arms 11 thus preventing them from flexing towards each other. Outwardly the resilient arms 11 are caught behind respective protrusions 15 in the carrier 7 in a manner to prevent translation of the plunger 9 in proximal direction P. The protrusions 15 are distally ramped in a manner to flex the resilient arms 11 inwards under load of the drive spring 8, which is prevented by the first boss 13 in the initial state.

The carrier 7 is locked to the chassis 2 near the proximal end P of the auto-injector 1 by two resilient clips 16 on the chassis 2 engaged in respective apertures 17 in the carrier 7. In the initial state the resilient clips 16 are outwardly supported by respective second bosses 18 in the trigger sleeve 12 so as to prevent the resilient clips 16 from flexing outwards and disengaging the carrier 7 from the chassis 2.

A control spring 19 in the shape of another compression spring is arranged around the carrier 7 and acts between a proximal collar 20 and a distal collar 21. The proximal collar 20 is mounted on a thread 22 on the carrier 7 (cf. FIG. 9) but is also splined to the trigger sleeve 12 by a pin 23 on the outer surface of the proximal collar 20 running in a first longitudinal groove 24 in the trigger sleeve 12 (cf. FIG. 10). Therefore the load from the proximal end of the control spring 19 is coupled through to the carrier 7 in the initial state. The distal collar 21 is coupled to the trigger sleeve 12 by a bayonet fitting but is also splined to the carrier 7, thus preventing the bayonet from releasing. The bayonet comprises a number of circumferentially arranged third bosses 25 on the inner surface of the trigger sleeve 12 and a corresponding number of circumferentially arranged fourth bosses 26 on the outer surface of the distal collar 21. In the initial state corresponding pairs of third bosses 25 and fourth bosses 26 are essentially aligned in a manner to abut against each other thus preventing translation of the distal collar 21 in distal direction D (cf. FIG. 10). The spline engagement comprises a number of longitudinal splines 27 on the carrier 7 each one engaged with a respective second longitudinal groove 28 on the inner surface of the distal collar 21 (cf. FIGS. 9 and 10) thus restricting relative rotation of the distal collar 21 and the carrier 7 and consequently preventing disengagement of the bayonet.

The trigger sleeve 12 is enabled to move in proximal direction P with respect to the carrier 7 against the force of the control spring 19. As the carrier 7 is initially locked to the chassis 2, translation of the trigger sleeve 12 in proximal direction P compresses the control spring 19, wherein the proximal collar 20 remains in the position of the initial state and wherein the distal collar 21 is translated with the trigger sleeve 12. The extension of the trigger sleeve 12 in distal direction D relative to the chassis 2 may be defined by a shoulder on the chassis 2 contacting a face on the trigger sleeve 12 (not illustrated).

A sequence of operation of the auto-injector 1 is as follows:

The protective needle shield 5 is removed from the proximal end P. The needle 4 is now exposed but still a safe distance back within the chassis 2 to protect the user from accidental needle stick injuries. The carrier 7 exhibits a retainer pocket 29 for accommodating a finger flange 30 of the syringe 3. The trigger sleeve 12 comprises a widened portion 31 for accommodating the retainer pocket 29 in a manner to restrict relative rotation of the trigger sleeve 12 and the carrier 7 while allowing translation in longitudinal direction. Thus rotation of the needle 4 is prevented.

Any axial load applied to the carrier 7 during removal of the protective needle shield 5 is resolved through the carrier 7 locked to the chassis 2 by the resilient clip 16. The chassis 2 abuts against the trigger sleeve 12 at a stop 35 in a manner to prevent further translation of the chassis 2 in proximal direction P. As the protective needle shield 5 is being removed axial load applied to the chassis 2 is thus resolved through the trigger sleeve 12 which would be held by a user. Removal of the protective needle shield 5 may be facilitated by a cap arranged on the proximal end P in the initial state, the cap engaged with the protective needle shield 5 (cap is not illustrated).

Figure 2B:
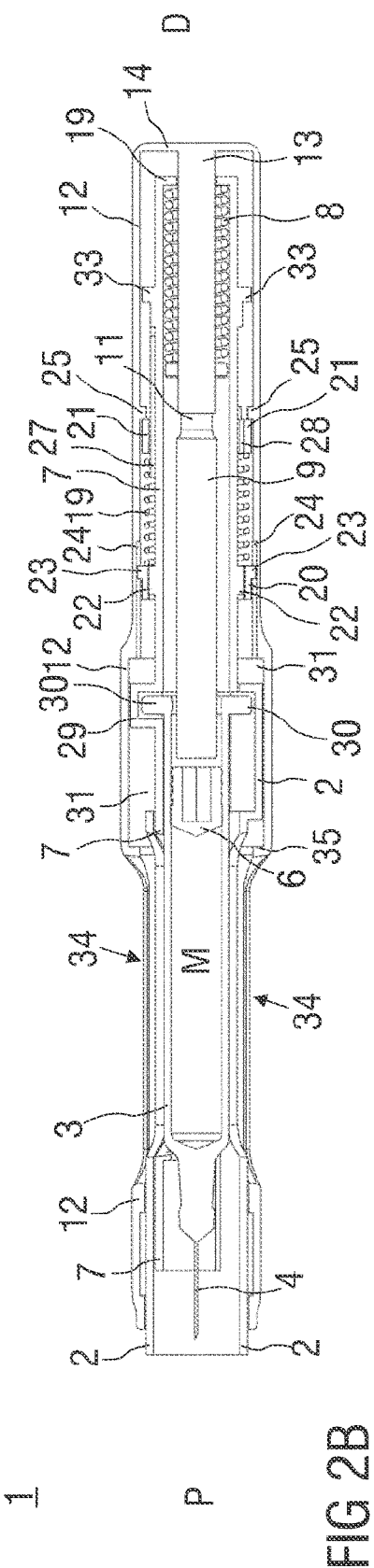

In order to trigger an injection, the user, i.e. the patient or a caregiver places the proximal end P of the auto-injector 1 on the injection site, e. g. the patient's skin and pushes the trigger sleeve 12 against the injection site (see FIG. 2). The chassis 2, together with all internal parts, translates in distal direction D into the trigger sleeve 12. The user would visualise this translation of the chassis 2 as depression of a skin-contact shroud. The control spring 19 opposes this motion but is specified such that its spring rate and preload are low enough for this to feel natural. This translation is completely reversible, i.e. the user can place the auto-injector on the injection site, depress the chassis 2 (skin-contact-shroud) and remove the auto-injector 1 from the injection site without activating it, thereby allowing the chassis 2 and the trigger sleeve 12 to return to their initial position under load of the control spring 19.

The auto-injector 1 may optionally have a two-stage firing mechanism. In this case, further translation from the position in FIG. 2 would be opposed by a detent mechanism (not illustrated).

When ready to do so, the user continues to push the proximal end P of the auto-injector against the injection site while holding the trigger sleeve 12. The chassis 2, together with all the internal parts locked to it moves relative to the trigger sleeve 12 in distal direction D until the carrier end face 10 comes into contact with the trigger end face 14 at the distal end D of the auto-injector 1 (see FIG. 3).

Figure 4A:
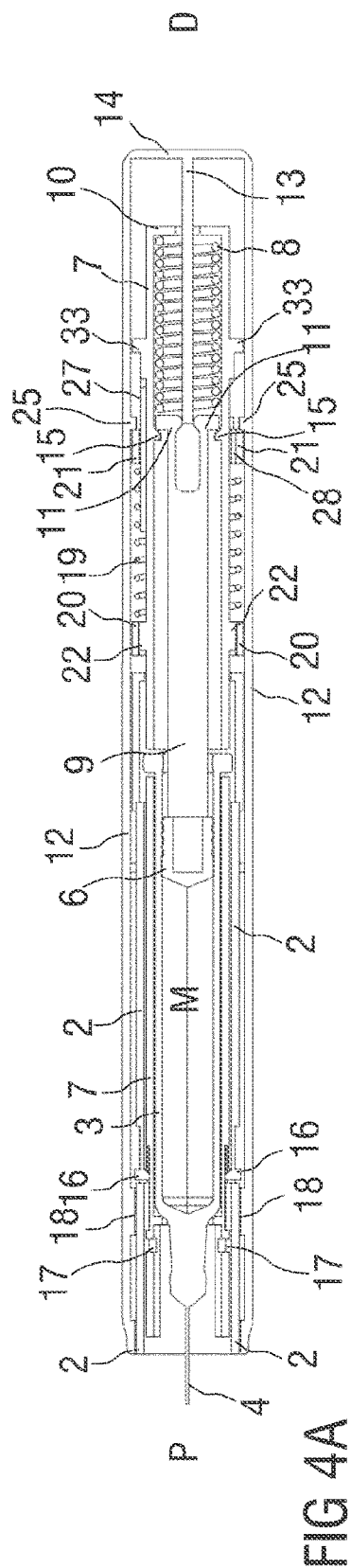
FIG. 4 is the auto-injector with an injection needle inserted into the injection site.
Figure 4B:
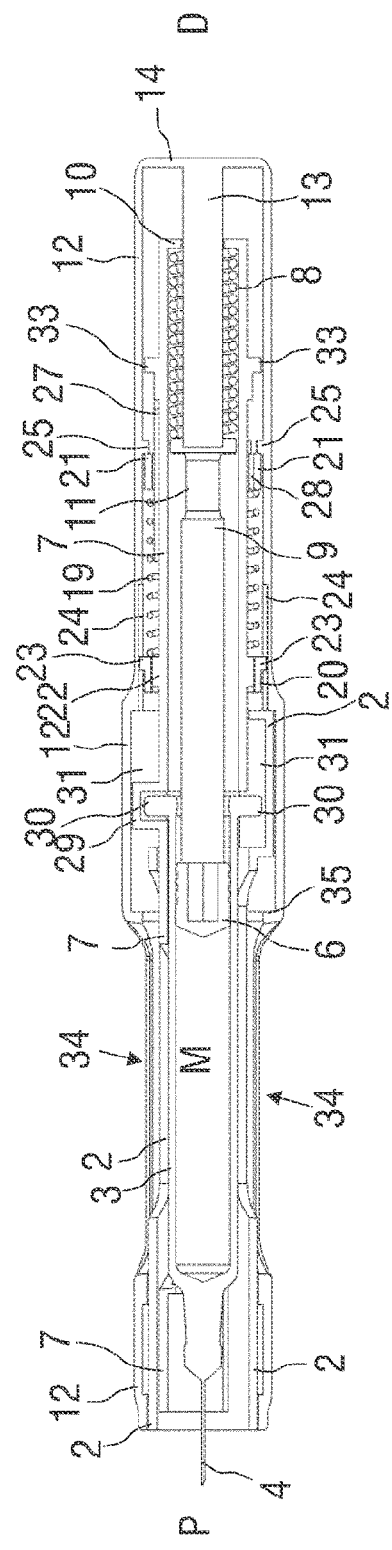

Just before this position is reached, the second boss 18 locking the carrier 7 to the chassis 2 has moved to a position where the resilient clip 16 is allowed to flex outwards due to its ramped engagement with the carrier 7, which is biased in proximal direction P by the control spring 19 pushing against the proximal collar 20. The lock between the chassis 2 and the carrier 7 is thus released. The control spring 19 then forces the carrier 7 to move in proximal direction P along with the syringe 3 and the needle 4 thus inserting the needle 4 into the injection site (see FIG. 4).

Figure 5A:
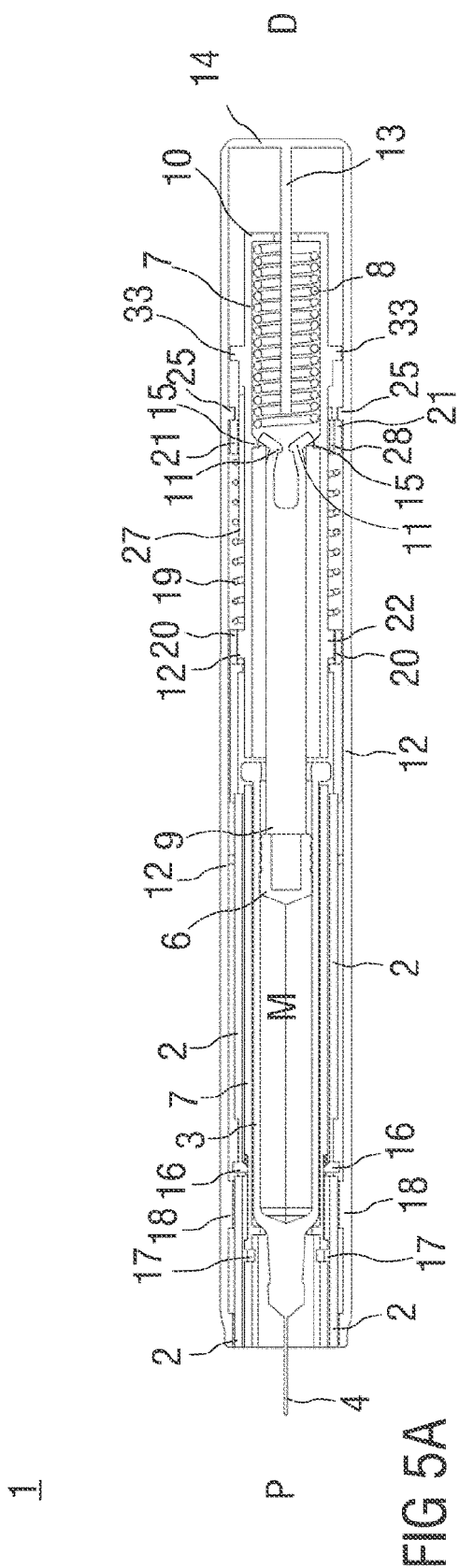
FIG. 5 is the auto-injector with a drive spring released for injection.
Figure 5B:
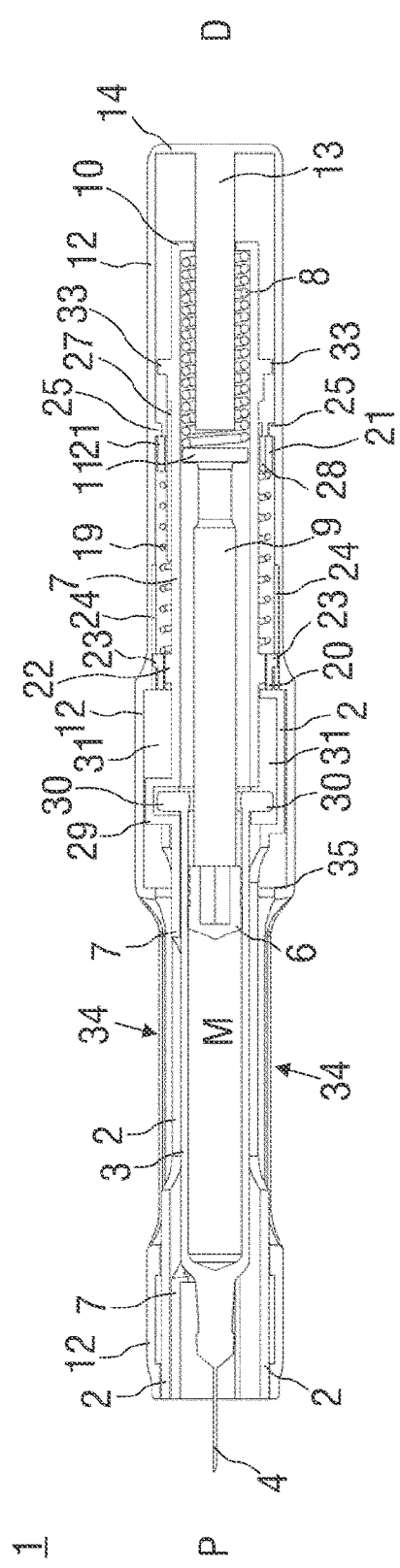

FIG. 5 shows the carrier 7, the syringe 3 and the needle 4 fully advanced into a maximum proximal position defining an injection depth. This maximum proximal position is limited by contact of the retainer pocket 29 with the chassis 2. Just before the maximum proximal position is reached, the carrier 7, syringe 3, needle 4, drive spring 8 and plunger 9 have translated relative to the trigger sleeve 12 so far that the first boss 13 is removed from between the resilient arms 11 thus releasing the plunger 9. The drive spring 8 pushes the resilient arms 11 over the protrusions 15 in proximal direction P due to their ramped engagement and the plunger 9 starts translating in proximal direction P under load of the drive spring 8. The drive spring 8 expands, the plunger 9 contacts the stopper 6 and the medicament M is expelled through the needle 4.

This motion of the stopper 6 continues until the stopper 6 bottoms out in the syringe 3, thereby fully emptying the syringe 3. The user would be asked to keep pressure on the injection site for a short period of time, e.g. ten seconds to ensure this is achieved (see FIG. 6).

As the user withdraws the auto-injector 1 from the injection site, the chassis 2 together with all internal components extend out of the trigger sleeve 12 in proximal direction D by the control spring 19 acting between the distal collar 21 locked to the trigger sleeve 12 and the proximal collar 20 locked to the carrier 7. The needle 4 is not yet withdrawn from the injection site during this motion since this would make the auto-injector 1 sensitive to the motion of the trigger sleeve 12 relative to the injection site during delivery of the medicament M, resulting in potential premature needle retraction should the user inadvertently move the auto-injector 1 slightly during the injection process. As a consequence of this feature the initial needle insertion depth does not rely upon full depression of the chassis 2 (skin interlock)—i.e. the insertion depth is defined with respect to the chassis 2.

The point at which retraction of the needle 4 is triggered is slightly before the chassis 2 has fully extended to the initial position to allow of part tolerance and ensure retraction always occurs before the chassis 2 stops moving relative to the sleeve trigger 12. However, it would be possible to configure the chassis 2 to have a more or less proximal position when removed from the injection site.

Figure 9:
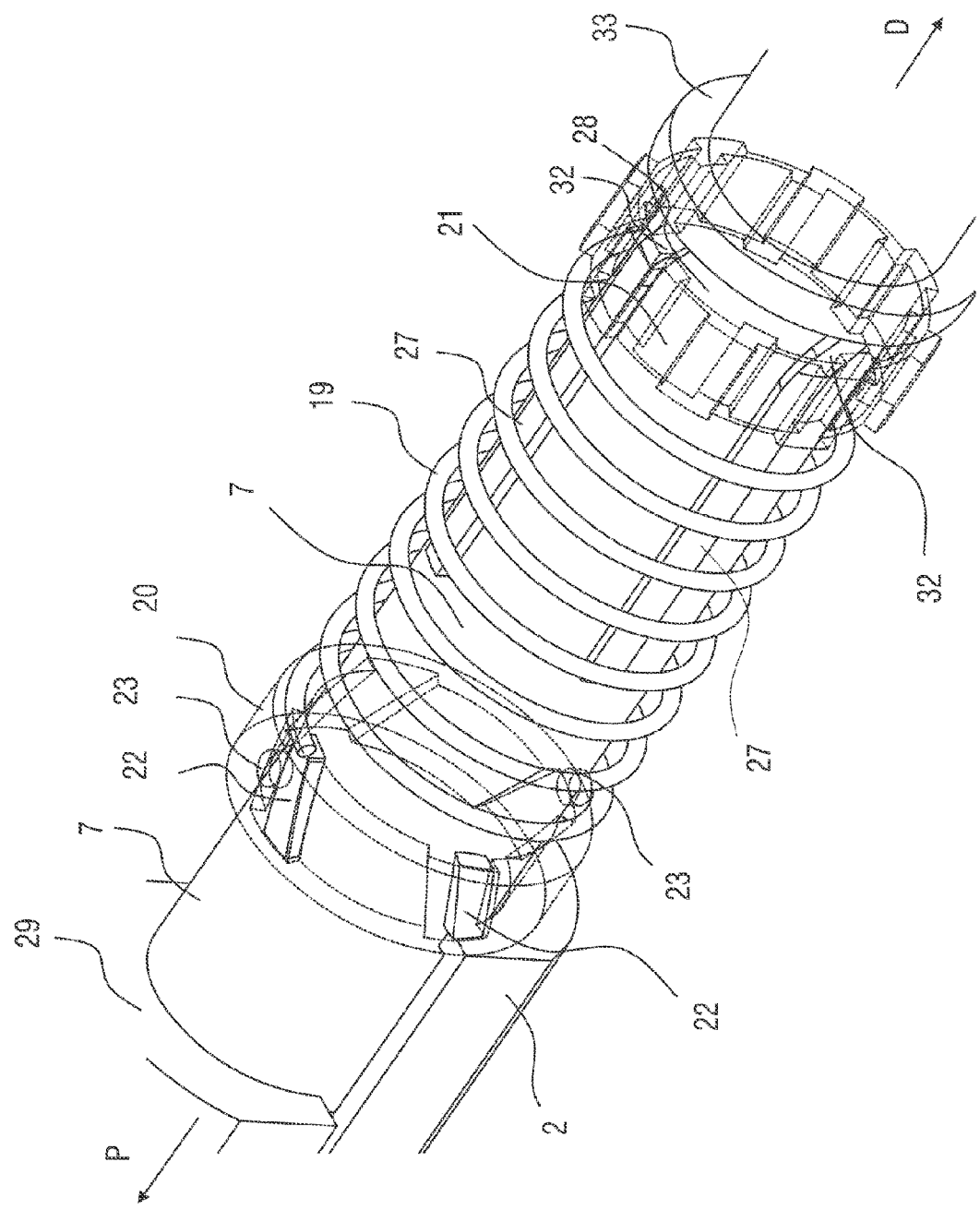
FIG. 9 is a detail view of the auto-injector with a control spring, a proximal collar and a distal collar in the state as in FIG. 7.

Just before the chassis 2 reaches the end of travel during this translation, the spline feature between the proximal collar 20 and the trigger sleeve 12 is released by the pin 23 of the proximal collar 20 travelling beyond the first longitudinal groove 24. This allows the proximal collar 20 to rotate on the thread 22 relative to the carrier 7. As the proximal collar 20 rotates it translates in proximal direction P relative to the carrier 7 and then decouples from it eventually coming in contact with the chassis 2 (see FIG. 7). Now the load on the proximal end of the control spring 19 is no longer applied to the carrier 7 but to the chassis 2. FIGS. 9 and 10 show the control spring 19, the proximal collar 20, and the distal collar 21 in this situation. Some components are drawn with dotted lines as transparent parts in order to make interactions comprehensible. It has to be understood that in reality these components do not need to be transparent.

As the chassis 2 continues to move in proximal direction P towards its final proximal position the distal collar 21 axially fixed relative to the trigger sleeve 12 moves along the spline 27 on the carrier 7. The spline 27, which is parallel to the longitudinal axis for the most part, ends with a lead screw thread 32. This causes the distal collar 21 to rotate relative to the carrier 7. As the distal collar 21 rotates, the bayonet coupling with the trigger sleeve 12 is released. The corresponding pairs of third bosses 25 and fourth bosses 26 become misaligned in a manner to allow the third bosses 25 to pass through gaps between the fourth bosses 26 and vice versa thus allowing translation of the distal collar 21 in distal direction D. The distal collar 21 contacts an external shoulder 33 on the carrier 7 thus resolving load from the distal end of the control spring 19 into the carrier 7.

Now acting between the carrier 7 and the chassis 2, the control spring 19 withdraws the carrier 7 inside the chassis 2, extracting the needle from the injection site in the process thus providing post injection needle safety. The auto-injector 1 may be configured to retract the carrier 7 until the carrier end face 10 abuts against the trigger end face 14. The carrier 7 may be locked to the chassis 2 at this point by a clip (not illustrated) to prevent it moving under inertial forces when heavily shaken.

If the user were to remove the auto-injector 1 from the injection site prior to full syringe emptying, the described motion of the chassis 2 would still be achieved. However, in that case the syringe 3 would be fully emptied after removal from the injection site.

The auto-injector 1 may optionally have a two-stage firing mechanism. In this case, in order to trigger an injection, the user, i.e. the patient or a caregiver places the proximal end P of the auto-injector 1 on the injection site, e. g. the patient's skin and pushes the trigger sleeve 12 against the injection site. The chassis 2, together with all internal parts, translates in distal direction D into the trigger sleeve 12 until further translation is prevented by a detent mechanism (not illustrated). The user would visualise this translation of the chassis 2 as depression of a skin-contact shroud. The control spring 19 opposes this motion but is specified such that its spring rate and preload are low enough for this to feel natural. This translation is completely reversible, i.e. the user can place the auto-injector on the injection site, depress the chassis 2 (skin-contact-shroud) up to the position of the detent and remove the auto-injector 1 from the injection site without activating it, thereby allowing the chassis 2 and the trigger sleeve 12 to return to their initial position under load of the control spring 19. Aside from the detent the operation of the auto-injector 1 is identical to the description above.

Viewing windows 34 are arranged in the shape of apertures in the trigger sleeve 12, in the chassis 2 and in the carrier 7 for inspecting the syringe contents.

The invention claimed is:

1. Auto-injector for administering a dose of a liquid medicament (M), comprising:
   a tubular chassis,
   a carrier subassembly comprising a tubular carrier slidably arranged relative to the chassis and partially arranged in the chassis, the carrier containing a syringe with a hollow injection needle, a drive spring and a plunger for forwarding load of the drive spring to a stopper of the syringe, wherein the syringe is locked for joint axial translation with the carrier,
   a wrap-over trigger sleeve arranged over the distal end (D) of the auto-injector, the trigger sleeve extending at least almost over the whole length of the auto-injector, wherein translation of the trigger sleeve relative to the chassis triggers needle insertion when an end face of the trigger sleeve contacts with an end face of the carrier,
   a control spring arranged around the carrier, wherein the control spring is configured to insert the needle and to retract the needle after administering the dose of the liquid medicament (M),
   a first interlock configured to couple a proximal end of the control spring to either the carrier for advancing it for needle insertion or to the chassis for needle retraction depending on the relative axial position of the carrier and the trigger sleeve,
   a second interlock configured to release the drive spring for injection when the carrier reaches an injection depth during needle insertion,
   a third interlock configured to couple the chassis to the carrier for joint axial translation relative to the trigger sleeve, wherein the third interlock is arranged to decouple the chassis from the carrier upon translation of the trigger sleeve in proximal direction (P) relative to the chassis thus releasing the control spring for needle insertion,
   a fourth interlock configured to couple a distal end of the control spring to either the carrier for needle retraction or to the trigger sleeve otherwise.

2. Auto-injector according to claim 1, wherein the first interlock comprises a proximal collar for transmitting load of the proximal end of the control spring, the proximal collar arranged to be engaged on a thread on the carrier in an initial state, the proximal collar having a pin arranged to be splined to a first longitudinal groove in the trigger sleeve in the initial state so as to prevent rotation of the proximal collar and couple it to the carrier, wherein the first longitudinal groove is arranged to release the pin upon translation of the chassis and carrier in proximal direction (P) under load of the control spring when the auto- injector is removed from the injection site thereby allowing rotation and translation of the proximal collar relative to the carrier under load of the control spring and subsequent abutting of the proximal collar against the chassis.

3. Auto-injector according to claim 1, wherein the second interlock comprises two resilient arms arranged distally on the plunger, the resilient arms exhibiting a thrust face for the drive spring, wherein a boss protrudes from a distal trigger end face of the trigger sleeve in proximal direction (P), wherein the boss is arrangeable between the two resilient arms thus preventing them from flexing towards each other, wherein protrusions are arranged in the carrier for respectively catching one of the resilient arms in a manner to prevent translation of the plunger in proximal direction (P), wherein the boss is arranged to be removed from between the resilient arms thus allowing them to flex inwards due to their ramped engagement to the protrusions under load of the drive spring and to release the plunger when the carrier reaches the injection depth during needle insertion.

4. Auto-injector according to claim 1, wherein the third interlock comprises at least one resilient clip on the chassis engageable in a respective aperture in the carrier, wherein at least one boss is arranged in the trigger sleeve for outwardly supporting the resilient clip so as to prevent the resilient clip from flexing outwards and disengaging the carrier from the chassis, wherein the boss is arranged to be removed from behind the resilient clip on translation of the trigger sleeve in proximal direction (P) relative to the chassis thereby allowing the resilient clip to flex outwards due to its ramped engagement with the carrier under load of the control spring.

5. Auto-injector according to claim 1, wherein the fourth interlock comprise a distal collar for transmitting load of the distal end of the control spring, the distal collar and the trigger sleeve having a bayonet fitting restricting translation of the distal collar relative to the trigger sleeve in distal direction (D) in at least one locked angular position of the distal collar and allowing translation of the distal collar relative to the trigger sleeve in distal direction (D) in at least one unlocked angular position of the distal collar, wherein the respective angular position is determined by a splined engagement of the distal collar with the carrier, wherein the distal collar is arranged to be rotated into the unlocked angular position upon translation of the chassis and carrier in proximal direction (P) under load of the control spring when the auto-injector is removed from the injection site thereby allowing translation of the distal collar relative to the trigger sleeve under load of the control spring in distal direction (D) and subsequent abutting of the distal collar against an external shoulder on the carrier for retraction.

6. Auto-injector according to claim 5, wherein the bayonet fitting comprises at least one circumferentially arranged first boss on the inner surface of the trigger sleeve and a corresponding number of circumferentially arranged second bosses on the outer surface of the distal collar, wherein in the locked angular position corresponding pairs of first bosses and second bosses are essentially aligned in a manner to abut against each other thus preventing translation of the distal collar in distal direction (D), wherein in the unlocked angular position corresponding pairs of first bosses and second bosses become misaligned in a manner to allow translation of the distal collar in distal direction (D).

7. Auto-injector according to claim 5, wherein the splined engagement comprises at least one longitudinal spline on the carrier engaged with a respective second longitudinal groove on the inner surface of the distal collar, wherein the spline is essentially parallel for maintaining the distal collar in the locked angular position but ends with a lead screw thread near its distal end for rotating the distal collar into the unlocked angular position.

8. Auto-injector according to claim 1, wherein a detent mechanism is provided for opposing translation of the chassis relative to the trigger sleeve for triggering needle insertion.

9. Method for operating an auto-injector, the auto-injector comprising:
a tubular chassis,
a carrier subassembly comprising a tubular carrier slidably arranged relative to the chassis and partially arranged in the chassis, the carrier containing a syringe with a hollow injection needle, a drive spring and a plunger for forwarding load of the drive spring to a stopper of the syringe, wherein the syringe is locked for joint axial translation with the carrier,
a wrap-over trigger sleeve arranged over the distal end (D) of the auto-injector, the trigger sleeve extending at least almost over the whole length of the auto-injector, wherein translation of the trigger sleeve relative to the chassis triggers needle insertion when an end face of the trigger sleeve contacts an end face of the carrier,
a control spring arranged around the carrier, wherein the control spring is configured to insert the needle and to retract the needle after administering a dose of a liquid medicament (M),
a first interlock configured to couple a proximal end of the control spring to either the carrier or to the chassis,
a second interlock configured to lock the drive spring,
a third interlock configured to couple the chassis to the carrier,
a fourth interlock configured to couple a distal end of the control spring to either the carrier or to the trigger sleeve,
the method comprising the steps of:
coupling the proximal end of the control spring to the carrier by the first interlock, preventing release of the drive spring by the second interlock, preventing decoupling of the chassis from the carrier by the third interlock and coupling the distal end of the control spring to the trigger sleeve in an initial state,
translating the trigger sleeve in proximal direction (P) relative to the chassis against the force of the control spring when the proximal end (P) of the auto-injector is being pushed against an injection site,
disengaging the third interlock when the trigger sleeve is at least almost fully translated thereby releasing the control spring for advancing the carrier subassembly for needle insertion,
releasing the drive spring by the second interlock when the needle reaches an injection depth during needle insertion, thereby allowing the drive spring to advance the plunger and the stopper for at least partially delivering the medicament (M),
translating the trigger sleeve in distal direction (D) under load of the control spring relative to the carrier subassembly on removal of the auto-injector from the injection site,
decoupling the proximal end of the control spring from the carrier and coupling it to the chassis by the first interlock and decoupling the distal end of the control spring from the trigger sleeve and coupling it to the carrier by the fourth interlock when the trigger sleeve reaches a defined position relative to the carrier,
retracting the carrier subassembly into the chassis into a needle safe position under load of the control spring.

10. Method according to claim 9, wherein the first interlock comprises a proximal collar for transmitting load of the proximal end of the control spring, wherein the proximal collar is engaged on a thread on the carrier in the initial state, wherein a pin on the proximal collar is splined to a first longitudinal groove in the trigger sleeve in the initial state so as to prevent rotation of the proximal collar and couple it to the carrier, wherein upon translation of the chassis and carrier in proximal direction (P) during removal of the auto-injector from the injection site the pin travels beyond a proximal end of the first longitudinal groove, thereby the control spring to rotate and translate the proximal collar relative to the carrier into a position where proximal collar abuts against the chassis.

11. Method according to claim 9, wherein the second interlock comprises two resilient arms arranged distally on the plunger, the resilient arms exhibiting a thrust face for the drive spring, wherein a boss protrudes from a distal trigger end face of the trigger sleeve in proximal direction (P), wherein the boss is arranged between the two resilient arms in the initial state thus preventing them from flexing towards each other, wherein protrusions are arranged in the carrier for respectively catching one of the resilient arms in a manner to prevent translation of the plunger in proximal direction (P), wherein the boss is removed from between the resilient arms when the carrier reaches the injection depth during needle insertion thus allowing the resilient arms to flex inwards due to their ramped engagement to the protrusions under load of the drive spring and to release the plunger.

12. Method according to claim 9, wherein the third interlock comprises at least one resilient clip on the chassis engaged in a respective aperture in the carrier in the initial state, wherein at least one boss is arranged in the trigger sleeve for outwardly supporting the resilient clip so as to prevent the resilient clip from flexing outwards and disengaging the carrier from the chassis in the initial state, wherein the boss is removed from behind the resilient clip on translation of the trigger sleeve in proximal direction (P) relative to the chassis, wherein the resilient clip is subsequently flexed outwards due to its ramped engagement with the carrier under load of the control spring.

13. Method according to claim 9, wherein the fourth interlock comprise a distal collar for transmitting load of the distal end of the control spring, the distal collar and the trigger sleeve having a bayonet fitting restricting translation of the distal collar relative to the trigger sleeve in distal direction (D) in at least one locked angular position of the distal collar and allowing translation of the distal collar relative to the trigger sleeve in distal direction (D) in at least one unlocked angular position of the distal collar, wherein the respective angular position is determined by a splined engagement of the distal collar with the carrier, wherein the distal collar is in the locked angular position in the initial state, wherein the distal collar is rotated into the unlocked angular position by the splined engagement upon translation of the chassis and carrier in proximal direction (P) when the auto- injector is removed from the injection site wherein the distal collar is subsequently translated in distal direction (D) relative to the trigger sleeve under load of the control spring into a position where it abuts against an external shoulder on the carrier which is then translated in distal direction (D) for retraction.

14. Method according to claim 13, wherein the bayonet fitting comprises at least one circumferentially arranged first boss on the inner surface of the trigger sleeve and a corresponding number of circumferentially arranged second bosses on the outer surface of the distal collar, wherein in the initial state the bayonet fitting is set in the locked angular position by essentially aligning corresponding pairs of first bosses and second bosses in a manner to abut against each other thus preventing translation of the distal collar in distal direction (D), wherein upon translation of the chassis and carrier in proximal direction (P) when the auto-injector is removed from the injection site the distal collar is rotated by the splined engagement into the unlocked angular position, thereby misaligning corresponding pairs of first bosses and second bosses in a manner to allow translation of the distal collar in distal direction (D).

15. Method according to claim 13, wherein the splined engagement comprises at least one longitudinal spline on the carrier engaged with a respective second longitudinal groove on the inner surface of the distal collar, wherein the second longitudinal groove is guided on an essentially parallel part of the spline in the initial state for maintaining the distal collar in the locked angular position wherein the second longitudinal groove is moved along the spline upon translation of the chassis and carrier in proximal direction (P) when the auto-injector is removed from the injection site and enters a lead screw thread near a distal end of the spline for rotating the distal collar into the unlocked angular position.

16. Auto-injector for administering a dose of a liquid medicament (M), comprising:
 a tubular chassis,
 a carrier subassembly comprising a tubular carrier slidably arranged relative to the chassis and partially arranged in the chassis, the carrier containing a syringe with a hollow injection needle, a drive spring and a plunger for forwarding load of the drive spring to a stopper of the syringe, wherein the syringe is locked for joint axial translation with the carrier,
 a wrap-over trigger sleeve arranged over the distal end (D) of the auto-injector, the trigger sleeve extending at least almost over the whole length of the auto-injector, wherein translation of the trigger sleeve relative to the chassis triggers needle insertion when an end face of the trigger sleeve contacts with an end face of the carrier,
 a control spring arranged around the carrier, wherein the control spring is configured to insert the needle and to retract the needle after administering the dose of the liquid medicament (M),
 a first interlock configured to couple a proximal end of the control spring to either the carrier for advancing it for needle insertion or to the chassis for needle retraction depending on the relative axial position of the carrier and the trigger sleeve,
 wherein the first interlock comprises a proximal collar for transmitting load of the proximal end of the control spring, the proximal collar arranged to be engaged on a thread on the carrier in an initial state, the proximal collar having a pin arranged to be splined to a first longitudinal groove in the trigger sleeve in the initial state so as to prevent rotation of the proximal collar and couple it to the carrier, wherein the first longitudinal groove is arranged to release the pin upon translation of the chassis and carrier in proximal direction (P) under load of the control spring when the auto- injector is removed from the injection site thereby allowing rotation and translation of the proximal collar relative to the carrier under load of the control spring and subsequent abutting of the proximal collar against the chassis,
 a second interlock configured to release the drive spring for injection when the carrier reaches an injection depth during needle insertion,
 a third interlock configured to couple the chassis to the carrier for joint axial translation relative to the trigger sleeve, wherein the third interlock is arranged to decouple the chassis from the carrier upon translation of the trigger sleeve in proximal direction (P) relative to the chassis thus releasing the control spring for needle insertion,
 a fourth interlock configured to couple a distal end of the control spring to either the carrier for needle retraction or to the trigger sleeve otherwise.

17. Auto-injector according to claim 16, wherein the second interlock comprises two resilient arms arranged distally on the plunger, the resilient arms exhibiting a thrust face for the drive spring, wherein a boss protrudes from a distal trigger end face of the trigger sleeve in proximal direction (P), wherein the boss is arrangeable between the two resilient arms thus preventing them from flexing towards each other, wherein protrusions are arranged in the carrier for respectively catching one of the resilient arms in a manner to prevent translation of the plunger in proximal direction (P), wherein the boss is arranged to be removed from between the resilient arms thus allowing them to flex inwards due to their ramped engagement to the protrusions under load of the drive spring and to release the plunger when the carrier reaches the injection depth during needle insertion.

18. Auto-injector according to claim 16, wherein the third interlock comprises at least one resilient clip on the chassis engageable in a respective aperture in the carrier, wherein at least one boss is arranged in the trigger sleeve for outwardly supporting the resilient clip so as to prevent the resilient clip from flexing outwards and disengaging the carrier from the chassis, wherein the boss is arranged to be removed from behind the resilient clip on translation of the trigger sleeve in proximal direction (P) relative to the chassis thereby allowing the resilient clip to flex outwards due to its ramped engagement with the carrier under load of the control spring.

19. Auto-injector according to claim 16, wherein the fourth interlock comprise a distal collar for transmitting load of the distal end of the control spring, the distal collar and the trigger sleeve having a bayonet fitting restricting translation of the distal collar relative to the trigger sleeve in distal direction (D) in at least one locked angular position of the distal collar and allowing translation of the distal collar relative to the trigger sleeve in distal direction (D) in at least one unlocked angular position of the distal collar, wherein the respective angular position is determined by a splined engagement of the distal collar with the carrier, wherein the distal collar is arranged to be rotated into the unlocked angular position upon translation of the chassis and carrier in proximal direction (P) under load of the control spring when the auto-injector is removed from the injection site thereby allowing translation of the distal collar relative to the trigger sleeve under load of the control spring in distal direction (D) and subsequent abutting of the distal collar against an external shoulder on the carrier for retraction.

20. Auto-injector according to claim 19, wherein the bayonet fitting comprises at least one circumferentially arranged first boss on the inner surface of the trigger sleeve and a corresponding number of circumferentially arranged second bosses on the outer surface of the distal collar, wherein in the locked angular position corresponding pairs of first bosses and second bosses are essentially aligned in a manner to abut against each other thus preventing translation of the distal collar in distal direction (D), wherein in the unlocked angular position corresponding pairs of first bosses and second bosses become misaligned in a manner to allow translation of the distal collar in distal direction (D).

* * * * *